United States Patent [19]

Pettrone et al.

[11] Patent Number: 5,114,850

[45] Date of Patent: May 19, 1992

[54] METHODS FOR PREPARING ACETATE ESTERS OF DIOLS AND POLYOLS USING CORYNEBACTERIUM OXYDANS IN SUBSTANTIALLY AQUEOUS MEDIA

[75] Inventors: Frank A. Pettrone; Gregory M. Whited; Charles T. Goodhue, all of Rochester, N.Y.

[73] Assignee: Eastman Kodak Company, Rochester, N.Y.

[21] Appl. No.: 542,290

[22] Filed: Jun. 22, 1990

[51] Int. Cl.$^5$ .................. C12P 7/62; C12P 19/02; C12N 1/04

[52] U.S. Cl. .................. 435/135; 435/105; 435/260

[58] Field of Search .............. 435/135, 105, 260

[56] References Cited

FOREIGN PATENT DOCUMENTS 0280232 8/1988 European Pat. Off. .

OTHER PUBLICATIONS

Klibanov, "Asymmetric Transformations Catalyzed by Enzymes in Organic Solvents"; Acc. Chem. Res. vol. 23, No. 4 (1990).
"Enzyme-Catalyzed Processes in Organic Solvents"; Proc. Natl. Acad. Sci. USA, vol. 82 pp. 3192-3196 (1985).
"Preparative Production of Optically Active Esters and Alcohols Using Esterase-Catalyzed Stereospecific Transesterification in Organic Media"; J. Am. Chem. Soc. vol. 106, pp. 2687-2692 (1984).
"Quantitative Analyses of Biochemical Kinetic Resolution of Emantiomers Z. Enzyme-Catalyzed Esterifications in Water-Organic Solvent Biphasic Systems", J. Am. Chem. Soc., vol. 109, pp. 2812-2817 (1987).
Dror et al., Enzyme Microb. Techno., vol. 12, (Apr. 1990), pp. 299-304.

Primary Examiner—David M. Naff
Assistant Examiner—Jon P. Weber
Attorney, Agent, or Firm—Judith A. Roesler

[57] ABSTRACT

Acetate esters of diols and polyols can be prepared in aqueous systems using a biocatalyst derived from *Corynebacterium oxydans*. The method involves the step of reacting a diol or polyol with an acetate ester in a substantially aqueous environment in the presence of said biocatalyst.

15 Claims, No Drawings

METHODS FOR PREPARING ACETATE ESTERS OF DIOLS AND POLYOLS USING CORYNEBACTERIUM OXYDANS IN SUBSTANTIALLY AQUEOUS MEDIA

FIELD OF THE INVENTION

This invention relates to a method of converting polyols and diols into acetate esters in substantially aqueous systems using a biocatalyst. In particular, the relevant biocatalyst is derived from Corynebacterium oxydans.

BACKGROUND OF THE INVENTION

The ability of lipases and proteases to catalyze the asymmetric hydrolysis of chiral esters in water is known. However, these known methods have inherent problems including the necessity of initially converting the racemic target molecule to an ester, the insolubility of most such esters in water and the sensitivity of many compounds to water. Therefore, it has been standard practice to use organic solvents in the reaction media for the catalysis of the asymmetric hydrolysis of chiral esters in water as shown in the "Asymmetric Transformations Catalyzed by Enzymes in Organic Solvents", Acc. Chem. Res., Vol. 23, No. 4 (1990) by Alexander M. Klibanov, Massachusetts Institute of Technology; "Enzyme-Catalyzed Processes in Organic Solvents", Proc. Natl. Acad. Sci. USA, Vol. 82, pp. 3192–3196 (1985); "Preparative Production of Optically Active Esters and Alcohols using Esterase-Catalyzed Stereospecific Transesterification in Organic Media," J. Am. Chem. Soc., Vol. 106, pp. 2687–2692 (1984) and "Quantitative Analyses of Biochemical Kinetic Resolution of Emantiomers Z. Enzyme-Catalyzed Esterifications in Water-Organic Solvent Biphasic Systems," J. Am. Chem. Soc., Vol. 109, pp. 2812–2817 (1987). Further, the acyl-enzyme intermediate in the above reaction is hydrolyzed in water, thereby regenerating the free enzyme and producing the acid. In principle, other nucleophiles may compete with water for covalent acyl-enzyme intermediate, but in aqueous solutions, hydrolysis prevails. On the other hand, if organic solvents are used as the reaction media, then the acyl-enzyme can be exposed to any nucleophile without competition from water, and therefore, hydrolysis can be replaced by a number of alternative reactions such as transesterification.

It is standard practice to prepare acetates of alcohols, diols and polyols from a variety of enzymes in organic solvents. Normally, this is done with the exclusion of water and even with the removal of water in order to drive the equilibrium to favor ester formation. This is true for both chemical and enzymatic synthesis.

It is usual in enzyme catalyzed reactions in water, when the water is in excess, that the water acts as the primary nucleophile. In this invention, even though the water is in excess, the organic diol or polyol is the primary nucleophile.

EP-A-0 280 232 (published Aug. 8, 1988) describes and claims the use of a biocatalyst derived from Corynebacterium oxydans to make a monoacetate by reacting a diol with an acetate ester. However, it simply describes a method that is carried out with a mixture of a diol, an acetate ester and a biocatalyst in an essentially all organic reaction medium.

U.S. Ser. No. 418,617 entitled "Methods for Preparing Polymerizable Monomers and Purified Transacylase from Corynebacterium Oxydans", commonly owned and assigned to Eastman Kodak Company, Rochester, N.Y., filed on Oct. 10, 1989 discloses a method for converting unsaturated esters into unsaturated polymerizable monomers using a biocatalyst derived from *Corynebacterium oxydans*. This method involves the step of reacting an unsaturated ester with an organic compound having a primary or secondary hydroxy group in a substantially organic environment in the presence of the noted biocatalyst.

While EP-A-0 280 232 and U.S. Ser. No. 418,617 describe important advances in the art, they fail to show how to prepare acetate esters from diols and polyols in substantially aqueous media. Because there is considerable unpredictability in the preparation of such esters, there is no certainty that the same procedures for preparing unsaturated polymerizable monomers from unsaturated esters or preparing a monoacetate from a diol can be used for preparing acetate esters from diols and polyols in substantially aqueous media.

Therefore, there continues to be a need for an economical and simple way to make acetate esters from diols and polyols by reacting a diol or polyol with an acetate ester in a substantially aqueous environment in the presence of a catalytic amount of a biocatalyst derived from *Corynebacterium oxydans*. For instance, there are situations whereby the alcohol substrates are not particularly soluble in organic solvents, for example, hydrophilic compounds like the sugars and pentaerythritol. Thus, it is desirable to be able to use a hydrophilic medium, i.e., aqueous medium, to run enzymatic reactions. Also, it is desirable to be able to run enzymatic esterifications of hydrophilic compounds, such as diols and polyols, e.g., sugars, in substantially aqueous media and take advantage of the chemoselectivity and steroselectivity of enzymes.

The catalytic activity of enzymes is well known. It is also well known that certain microorganisms possess enzymes which can be used as biocatalysts outside of the host to prepare useful compounds from starting materials that act as substrates for the enzymes.

In fact, EP-A-0 280 232 (published Aug. 8, 1988) discussed above discusses the catalytic activity of an enzyme produced by *Corynebacterium oxydans* in the process of making a monoacetate by reacting a diol with an acetate ester. Moreover, U.S. Ser. No. 229,959 (filed Aug. 9, 1988 by Green, Goodhue and Olyslager) describes and claims the use of a biocatalyst derived from *Corynebacterium oxydans* to make a chiral hydroxycarboxylic acid from a prochiral diol.

Biocatalysis is also described for a porcine pancreatic lipase by Zaks et al (*Science*, 224, pp. 1249–1251, 1984). A strain belonging to the genus Corynebacterium is known to provide certain fatty acids from an n-paraffin according to U.S. Pat. No. 3,823,070. Alkenes are oxidized by a strain of *Methylococcus capsulatus* according to U.S. Pat. No. 4,594,324. Other biocatalytic reactions, including the production of optically active compounds, are described for example in U.S. Pat. No. 4,008,125 and U.S. Pat. No. 4,415,657.

Summary of the Invention

The problems noted above are overcome and a significant advance in the art of biocatalysis is provided by a method for the preparation of an acetate ester of diols and polyols, the method comprising the step of reacting a diol or polyol with an acetate ester in a substantially aqueous environment in the presence of a catalytic amount of a biocatalyst derived from *Corynebacterium oxydans*.

The reaction taught in EP-A-0 280 232 (published Aug. 8, 1988) requires only a small amount of water. An example discloses about 8% by volume of water to about 92% by volume of ethyl acetate. It is further stated the reaction requires only a small amount of water. Water is present up to its saturation point in the ester. This is distinguished from the donating ester saturated water of this invention which depends on the saturation of water by ethyl acetate, not the saturation of ethyl acetate by water. EP-A-0280 232 cited above does not teach a method whereby an enzyme catalyzes the attack of a diol/polyol nucleophile on an ester in preference to water (by which the acyl-enzyme produced in the reaction of this invention is able to be exposed to a nucleophile in a substantially aqueous environment without competition from water) as does the method of the present invention.

U.S. Ser. No. 418,617 entitled "Methods for Preparing Polymerizable Monomers and Purified Transacylase from Corynebacterium Oxydans" assigned to Eastman Kodak Company, Rochester, N.Y., filed on Oct. 10, 1989 discussed above clearly states that the environment of the reaction disclosed is substantially organic, meaning that less than about 10% (by volume) of water is present. The examples disclose a ratio of about 3 to 7% by volume of water to about 97 to 93% volume of acetate ester. Therefore, U.S. Ser. No. 418,617 does not teach the method of the present invention.

DETAILED DESCRIPTION OF THE INVENTION

The compounds which are produced in the method of the present invention are useful as intermediates in the synthesis of other compounds. The acetate esters of the diols can be further converted using conventional reactions into other optically active intermediates. For example, the remaining hydroxyl group can be converted to halo such as chloro, bromo or iodo, azido, phthalimido, cyano and carboxyl.

The biocatalyst used in the practice of this invention is derived from *Corynebacterium oxydans*. By "derived from" is meant that any composition that is made from this species of microorganism that catalyzes the reaction defined herein can be used. Useful compositions include a culture medium containing the cells, the recovered cells themselves, or extracts from the cells (such as an at least partially purified enzyme) which include the necessary catalytic activity. The method need not be carried out in the presence of viable cells as in a fermentation. The composition is used as the catalyst in the reaction.

The isolation, maintenance and characterization of a typical *Corynebacterium oxydans* is known in the art, such as the procedures described in U.S. Pat. No. 3,558,431. *Corynebacterium oxydans* is sometimes known in the art as *Flavobacterium oxydans*. Several strains of this microorganism are useful in the practice of this invention, namely ATCC No. 53586 (deposited Feb. 11, 1987), ATCC No. 21245, (deposited May 6, 1968) and ATCC No. 53587 (deposited Feb. 11, 1987) (American Type Culture Collection, 12301 Parklawn Drive Rockville, Md. 20852). The strain identified as ATCC No. 53586 is preferred. The preparation of a useful composition of whole cells is described hereinafter.

In a preferred embodiment, the biocatalyst is an at least partially purified transacylase derived from a strain of *Corynebacterium oxydans*, such as from the strains identified above. This enzyme extract is useful in the preparatory method of this invention, and particularly in the bioconversion reaction of the esters described herein with the preferred diols or polyols, including but not limited to, 2,2-dimethyl-1,3-propanediol, ethylene glycol, glycerol, 1,6-hexanediol, cis- or trans-cyclohexanedimethanol, 2,2'-oxydiethanol, 2-allyl-1,3-propanediol, D-glucal and D-galactal. Specific cell growth and transacylase isolation and purification techniques are outlined in more detail hereinafter.

Other strains of this species, not specifically identified herein, are believed to be useful as well. Any strain which will convert the diol or polyol into the acetate ester as defined herein is useful in this invention. It would require only routine experimentation for a skilled worker in the art to determine if a particular strain was useful. Such experimentation would involve following the simple procedure outlined hereinafter and analyzing the products to identify them. If an acetate ester is produced, the strain used in the reaction is a biocatalyst contemplated by this invention.

The method of this invention is stereoselective in that only one hydroxy group of two equivalent hydroxy groups in a diol is preferentially esterified; or the primary hydroxyl group in a polyol undergoes esterification much more rapidly than a secondary or tertiary hydroxyl group. Primary, secondary and tertiary hydroxyl groups have the art understood definition.

In the practice of this invention, the esters which are useful include any acetate ester, such as ethyl, methyl, butyl and vinyl acetate and others which would be readily apparent to one skilled in the art. The esters have a leaving group on the other side of the carbonyl group which includes the oxy linkage adjacent to the carbonyl. By "leaving group" is meant the group which is cleaved from the donor ester upon attack by the diol/polyol nucleophile.

The diols and polyols useful in the practice of this invention can be any compound which has at least one primary or secondary (and preferably, primary) hydroxy group which will act as a nucleophile to undergo nucleophilic acyl substitution with the ester defined above. Primary and secondary hydroxy groups have the art understood definition.

More specifically, diols useful in the practice of this invention have the structure:

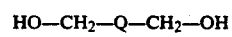

HO—CH$_2$—Q—CH$_2$—OH wherein Q is a divalent aliphatic, alicyclic or aromatic moiety having a molecular weight of from about 0 to about 200.

The term aliphatic is defined as a saturated or unsaturated straight chain moiety made up of any number of carbon, hydrogen, nitrogen, oxygen, phosphorous or sulfur atoms in the backbone, and having any number of substituents chosen from alkyl groups of 0 to 10 carbon atoms, halo (such as chloro or bromo), alkoxy having from 0 to 10 carbon atoms or amino. Generally, the aliphatic group comprises one or more substituted or unsubstituted alkylene groups interrupted by heteroatoms (such as oxygen, sulfur, nitrogen or phosphorus). The term alicyclic refers to a nonaromatic, saturated or unsaturated cyclic group having from 3 to 8 carbon and heteroatoms, and includes carbocyclic moieties (such as cyclopentyldimethylene, cyclohexyldimethylene and others readily apparent to one skilled in the art) and heterocyclic moieties (such as tetrahydrofurfuryl, tetrahydropyranedimethylene and tetrahydrothiophenedimethylene). Divalent aromatic moieties include those having from 6 to 14 carbon and heteroatoms which possess aromaticity as that term is understood in the art. Useful aromatic moieties include phenyldimethylene, pyridyldimethylene, chloropyridyldimethylene, pyridoxinyl and thiophenedimethylene.

More preferably, Q is a linear chain alkane of 0-4 carbons or branched derivatives thereof, wherein the alkane can be unsubstituted or substituted.

In some instances, the diol is prochiral or chiral or a racemic mixture thereof (such as 2-phenyl-1,3-propanediol and 2-isopropyl-1,3-propanediol).

Representative diols useful in this invention include, but are not limited to, 2,2-dimethyl-1,3-propanediol, 2-methyl-1,3-propanediol, 1-phenyl-1,3-propanediol, 1,4-butanediol, 1,5-pentanediol, 1,3-propandiol, 1,6-hexanediol, ethylene glycol, cis, trans-cyclohexandedimethanol, 2,2'-oxydiethanol, 2-alkyl-1,3-propanediol and 2-propyl-1,3-propanediol. Particularly useful diols include 2,2-dimethyl-1,3-propandiol, ethylene glycol, 1-phenyl-1,3-propandiol, 1,3-propandiol, and 2-alkyl-1,3-propanediol.

Representative polyols include trihydroxymethylmethane, pentaerythritol, polyethylene glycol and monosaccharides, such as mannose, galactose, D-glucal, D-galactal, etc. Preferred polyols are D-glucal and D-galactal.

The present method is carried out with a mixture of one or more acetate esters, one or more diols or polyols in the presence of the biocatalyst described above. The environment of the reaction mixture is substantially aqueous meaning that the reaction mixture contains water saturated with the donor ester. The amount of the donor ester that can be dissolved in water depends on the ester structure, and the temperature and pressure of the reaction mixture. The ratio of acetate ester to water is generally about 1-10% by volume of acetate ester to generally about 90-99% by volume of water. The preferred ratio of acetate ester to water is generally about 3-8% by volume of acetate ester to generally about 92-97% by volume of water.

The ratio of the reactants in the reaction mixture can vary widely, and one skilled in the art can optimize the ratio for given reactants to obtain optimum yields with routine experimentation. Generally, the volume ratio of acetate ester to diol or polyol is from about 1:1 to about 100:1. A ratio of from about 2:1 to about 4:1 is preferred.

The amount of biocatalyst is also widely variable with optimum amounts readily discoverable with minimal experimentation. Thus, a catalytic amount would vary depending upon the amounts of reactants, the conditions of reaction and the purity of the transacylase or concentration of whole cells. Generally, the biocatalyst is present in the reaction solution in an amount of from about 0.5 to about 5% (by weight) for dry whole cells, with from about 1 to about 2% (by weight) being preferred. When at least partially purified transacylase is used, substantially less amounts are needed for acceptable bioconversion.

The reaction mixture can optionally contain small amounts of other materials. For example, a small amount of acid or base can be added to adjust the pH if necessary.

The reaction conditions are not critical. The temperature is generally in the range of from about 5° C. to about 65° C., with from about 25° C. to about 35° C. being preferred. The pH of the mixture (if any water is present) is generally from about 5 to about 11. Reaction times can vary depending upon the reactants and yields desired, with times between about 15 min. and about 72 hours being typical.

PREPARATION OF ACETATE SATURATED WATER SOLUTION

The acetate saturated water solution was prepared by mixing equal volumes of the appropriate acetate ester and water, and vigorously stirring the mixture at 20°-25° C. for about 30 minutes. The mixture was transferred to a separatory funnel, and the organic and aqueous layers allowed to separate. The bottom aqueous layer was drawn off and used. When using vinyl acetate as the ester, the solution contained about 3-3.5% (by volume) of vinyl acetate.

PREPARATION OF BIOCATALYST COMPOSITION

A biocatalytic composition containing whole cells useful in the practice of this invention can be prepared as follows. Cells of *C. oxydans* (ATCC 53586) were grown in common mineral salt medium (see for example, Stanier et al, *J. Cell Comp. Phys.*, 49, p. 25, 1957) containing yeast extract (0.05%, from Difco Laboratories) and succinic acid (1%). After 24-72 hours, the cells were harvested, washed with water, lyophilized and stored at 4° C. as a powder.

ISOLATION AND PURIFICATION OF TRANSACYLASE FROM *CORYNEBACTERIUM OXYDANS*

This example illustrates the procedure for isolating and at least partially purifying a transacylase from *Corynebacterium oxydans*. This transacylase has been found to be a biocatalyst in the practice of the method of this invention. (see Examples below).

Materials and Methods

*C. oxydans* cells (ATCC 53586) were grown in a mineral salt medium containing yeast extract (0.05%) and succinate (1%). The cells were harvested at late log phase, washed, lyophilized and stored at 4° C.

Standard chromatography media, phenyl sepharose, DEAE sepharose and S-300 sephacryl were obtained from Pharmacia Chemical Co. DNase and bovine serum albumin were obtained from Sigma Chemical Co. Bicinchoninic acid protein assay reagents and N,O-bis(trimethylsilyl)trifluoracetamide silylation reagent were purchased from Pierce Chemical Co. All other reagents and chemicals were obtained from Eastman Kodak Co. or other chemical companies in the highest purity available.

Protein determinations were performed using the Bicinchoninic Acid Protein reagent according to the manufacturer's instructions. Bovine serum albumin was used as the standard, the concentration of which was determined spectrophotometrically.

In the gas chromatography assay of the enzyme, cell extract (15 μl) was added to ethyl acetate (200 μl) containing 2,2-dimethyl-1,3-propanediol (108 mmolar) and the resulting mixture was incubated at 30°-37° C. with shaking for an appropriate time. The reaction was stopped by the addition of silylation reagent:pyridine (1:1) and heating at 60° C. for 20 minutes. Product formation was determined by capillary gas chromatography.

Column chromatography was carried out isothermally at 150° C. on a 25M AQ3-BP5, 1 μm column from Scientific Glass Engineering, Inc. The detection was accomplished using a standard flame ionization detection procedure. Since none of the substrate or product is metabolized during the reaction, the ratio of the substrate and product peaks can be used to calculate the product formed without a calibrated instrument or internal standard. Assays of column fractions were done at different times and temperatures, as appropriate. Enzyme activity is expressed in Units/mg protein. One Unit is the amount of enzyme required to convert one μmole of substrate to product in one minute at 30° C.

ISOLATION OF CELL EXTRACT

All procedures were conducted at room temperature unless otherwise noted. A cell free extract was prepared by suspending cells (20 g) in potassium phosphate buffer (400 ml, 100 mmolar, pH 7) containing DNase (0.002%). The resulting mixture was sonicated on ice with stirring at 5 amp for 15 minutes (that is, 30 minutes pulsed at 50% of the duty cycle). The sonicated suspension was centrifuged at 25,000×g for 20 minutes. The resulting supernatant was a cell free extract of *C. oxydans*.

PURIFICATION OF TRANSACYLASE

The cell free extract obtained above was centrifuged at 100,000×g for one hour and the supernatant was then used for further purification. Ammonium sulfate was added slowly over 30 minutes to a final concentration of 435 mmolar, and the precipitate formed was removed by centrifugation at 25,000×g for 20 minutes.

This extract was chromatographed on phenyl sepharose in the following manner: A phenyl sepharose column (500 mm in diameter and 70 mm in height) was equilibrated in potassium phosphate buffer (100 mmolar, pH 7.5) containing ammonium sulfate (425 mmolar). The column was pumped at 3 ml/min., 12 ml fractions were collected, and the absorbance was monitored at 280 nm. The supernatant from the cell free extract which had been centrifuged at 100,000×g (350 ml) containing ammonium sulfate (425 mmolar) was loaded on the column and unbound protein washed away with the above equilibrating buffer (240 ml). A 360 ml gradient from the equilibrating buffer to potassium phosphate buffer (10 mmolar, pH 6.5) was run followed by a 360 ml gradient to the same buffer containing ethanol (5%). Final conditions were maintained for 360 ml. Various fractions were assayed for transacylase activity using gas chromatography.

Fractions from the column chromatography containing enzyme activity (65-85) were pooled and the pH of the resulting extract was adjusted to 8.

This extract was then chromatographed on DEAE sepharose in the following manner: A DEAE sepharose column (50 mm in diameter and 70 mm in height) was equilibrated in tris(hydroxymethyl)aminomethane buffer (20 mmolar, pH 8). The column was pumped at 4 ml/min., 12 ml fractions were collected and the absorbance was monitored at 280 nm. Pooled fractions (240 ml) from the phenyl sepharose column, adjusted to pH 8, were loaded and the unbound protein was washed away with equilibrating buffer (120 ml). A 600 ml gradient to equilibrating buffer containing potassium chloride (500 mmolar) was run followed by maintaining final conditions for 480 ml. Various fractions were assayed for transacylase activity using gas chromatography.

Fractions containing transacylase activity (88-92) were pooled and the protein concentrated by precipitation with ammonium sulfate (70% saturation). The precipitated protein was collected by centrifugation and resuspended in potassium phosphate buffer (2 ml, 100 mmolar, pH 7).

This extract was separated by size exclusion chromatography in the following manner: A S-300 sephacryl column (26 mm in diameter by 900 mm in height) was equilibrated in potassium phosphate buffer (100 mmolar, pH 7). The column was pumped at 18 ml/hour, 4.5 ml fractions were collected and the absorbance was monitored at 280 nm. Active fractions, concentrated from DEAE chromatography (2.0 ml), were loaded on the column and the protein eluted with equilibrating buffer. Certain fractions were assayed for transacylase activity using gas chromatography.

Fractions containing transacylase activity from the foregoing chromatography (62-66) were pooled. The following Table comprises a summary of the purification procedure and the transacylase activity of the various extracts.

TABLE

| Extract | Protein | | | Transacylase Activity | | | | | |
|---|---|---|---|---|---|---|---|---|---|
| | Volume (ml) | mg/ml | Total (mg) | Units/ ml | Total Units | Specific Activity (Units/mg Protein) | % of Total | % of Previous Step | Purification Fold* |
| Cell free extract | 376 | 10.3 | 3873 | 2.09 | 823 | 0.20 | 100 | — | 1 |
| Centrifuged supernatant | 356 | 9.81 | 3492 | 2.01 | 762 | 0.21 | 93 | 93 | 1.1 |
| Fractions from Phenyl Sepharose Chromatography | 245 | 1.23 | 301 | 2.10 | 537 | 1.72 | 65 | 70 | 0.9 |
| Fractions from DEAE Sepharose Chromatography | 48 | 0.87 | 41.8 | 5.83 | 280 | 6.69 | 34 | 52 | 33.5 |
| Fractions from S-300 Size Exclusion Chromatography | 21.4 | 0.64 | 13.7 | 7.34 | 157 | 11.5 | 19 | 56 | 57.5 |

*This is a common term describing the ratio of specific activities.

The following examples are presented for illustrative purposes. It is understood that other reactants and microbial strains could be used. Any needed modifications to the procedures for given reactants would be readily apparent to one skilled in the art in view of this teaching. All percentages of materials in this application are by weight unless otherwise indicated.

EXAMPLE 1

Preparation of Monoacetate of 2,2-Dimethyl-1,3-propanediol Using Whole Cells

This example illustrates the practice of this invention to prepare a monoacetate of a diol using whole cells containing *C. oxydans.*

A mixture of 2,2-dimethyl-1,3-propanediol (0.104 g, 1 mmol) and whole cells (0.1 g), containing *C. oxydans*, in vinyl acetate saturated water (10 mL, prepared as described above) was shaken in a stoppered flask at 30° C. at 300 RPM for 48 hours. The reaction was monitored by gas chromatography.

The monoacetate of 2,2-dimethyl-1,3-propanediol was formed in 66.1% yield. Product identification was done by gas chromatography by comparison with the known compound.

EXAMPLE 2

Preparation of Monoacetate of 2,2-Dimethyl-1,3-propanediol Using Partially Purified Enzyme Using Vinyl Acetate This example illustrates the practice of this invention to prepare a monoacetate of a diol using a partially purified transacylase enzyme.

A mixture of 2,2-dimethyl-1,3-propanediol (4.58 mg), vinyl acetate saturated water (458 μL) and enzyme solution (32 μL, containing about 7 units of enzyme/mL of potassium phosphate buffer, 100 mmolar, pH 7.5) was placed in a sealed vial and shaken at 30° C. at 300 RPM for 18.5 hours. The reaction was monitored by gas chromatography.

The monoacetate of 2,2-dimethyl-1,3-propanediol was formed in 84.2% yield. Product identification was done by gas chromatography by comparison with the known compound.

EXAMPLE 3

Preparation of Monoacetate of 2,2-Dimethyl-1,3-propanediol Using Partially Purified Enzyme Using Ethyl Acetate A mixture of 2,2-dimethyl-1,3-propanediol (4.58 mg), ethyl acetate saturated water (458 μL) and enzyme solution (32 μL, containing about 7 units of enzyme/mL of potassium phosphate buffer, 100 mmolar, pH 7.5), was placed in a sealed vial and shaken at 30° C. at 300 RPM for 18.5 hours. The reaction was monitored by gas chromatography.

The monoacetate of 2,2-dimethyl-1,3-propanediol was formed in 21.3% yield. Product identification was done by gas chromatography by comparison with the known compound.

EXAMPLE 4

Preparation of an Optically Active Monoacetate from a Prochiral Diol

This example illustrates the preparation of an optically active monoacetate from a prochiral diol using whole cells containing *C. oxydans.*

A mixture of 2-allyl-1,3-propanediol (0.116 g, 1 mmol), whole cells containing *C. oxydans* (0.1 g) and vinyl acetate saturated water (20 mL) was shaken at 30° C. and 300 RPM for 48 hours. The optically active monoacetate of 2-allyl-1,3-propanediol was obtained in 85% yield. Structure determination was done by nuclear magnetic resonance.

EXAMPLE 5

Preparation of a Monoacetate of a Polyol Using Partially Purified Enzyme

This example illustrates the chemoselective esterification of a primary alcohol in a polyol containing both primary and secondary hydroxy groups. The substrate used was D-glucal, having the following structure:

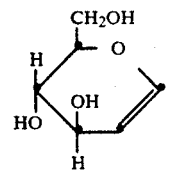

The reaction was run as described using 458 μL of a solution of D-glucal (100 mmolar) in vinyl acetate saturated water and 32 μL of enzyme solution. After 48 hours, the yield of the monoacetate of D-glucal was 13.4%. Structure and mass determination was done by gas chromatography and mass spectrometry.

EXAMPLE 6

Preparation of a Monoacetate of a Polyol Using Partially Purified Enzyme

This example illustrates the chemoselective esterification of a primary alcohol in a polyol containing both primary and secondary hydroxy groups. The substrate used was D-galactal, having the following structure:

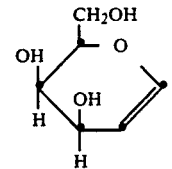

The reaction was run as described using 458 μL of a solution of D-galactal (100 mmolar) in vinyl acetate saturated water and 32 μL of enzyme solution. After 48 hours, the yield of the monoacetate of D-glucal was 32%. Structure and mass determinations were done by gas chromatography, mass spectrometry and nuclear magnetic resonance, and indicated that only the primary hydroxyl group had been acylated.

The invention has been described in detail with particular reference to certain preferred embodiments thereof, but it will be understood that variations and modifications can be effected within the spirit and scope of the invention.

What is claimed is:

1. A method for the preparation of an mono-acetate ester of diols and polyols, said method comprising the step of reacting an diol or polyol with an acetate ester in a aqueous environment, wherein the ratio of acetate ester to water is about 1–10% by volume of acetate ester to about 90–99% by volume of water, and in the presence of a catalytic amount of a biocatalyst derived from *Corynebacterium oxydans*.

2. The method of claim 1 wherein said diol has the structure:

$$HO-CH_2-Q-CH_2-OH$$

wherein Q is a divalent aliphatic, alicyclic or aromatic moiety having a molecular weight of from about 0 to about 200.

3. The method of claim 2 wherein Q is a linear or branched chain alkane having 0 to 4 carbon atoms.

4. The method of claim 2 wherein said diol is a prochiral or chiral diol or a racemic mixture thereof.

5. The method of claim 1 wherein said polyol is selected from the group consisting of trihydroxymethylmethane, pentaerythritol, polyethylene glycol, glycerol and monosaccharides.

6. The method of claim 1 wherein said polyol is D-glucal or D-galactal.

7. The method of claim 1 wherein said acetate ester is vinyl acetate.

8. The method of claim 1 wherein the diol or polyol contains at least one primary hydroxyl group.

9. The method of claim 1 wherein said acetate ester is ethyl acetate.

10. The method of claim 1 wherein the ratio of acetate ester to water is about 3–8% by volume of acetate ester to about 92–97% by volume of water.

11. The method of claim 1 wherein the volume ratio of the acetate ester to diol or polyol is from about 1:1 to about 100:1.

12. The method of claim 1 wherein the volume ratio of the acetate ester to diol or polyol is from about 2:1 to about 4:1.

13. The method of claim 1 carried out at a temperature in the range of from about 5° C. to about 65° C.

14. The method of claim 1 wherein said biocatalyst is provided in whole cells of *Corynebacterium oxydans*.

15. The method of claim 1 wherein said biocatalyst is provided as an at least partially purified transacylase derived from *Corynebacterium oxydans*.

* * * * *